(12) United States Patent
Porter et al.

(10) Patent No.: US 8,852,559 B2
(45) Date of Patent: Oct. 7, 2014

(54) BORINIC COMPOSITIONS

(75) Inventors: Venda Porter, Piscataway, NJ (US); Andre Morgan, Robbinsville, NJ (US); Stanislav Jaracz, Somerset, NJ (US); Jennifer Gronlund, Flemington, NJ (US); Guofeng Xu, Plainsboro, NJ (US); Donghui Wu, Bridgewater, NJ (US); Michael Prencipe, Princeton Junction, NJ (US); Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/319,802

(22) PCT Filed: Jun. 3, 2010

(86) PCT No.: PCT/US2010/037220
§ 371 (c)(1),
(2), (4) Date: Nov. 10, 2011

(87) PCT Pub. No.: WO2010/141693
PCT Pub. Date: Dec. 9, 2010

(65) Prior Publication Data
US 2012/0064017 A1    Mar. 15, 2012

Related U.S. Application Data (60) Provisional application No. 61/183,788, filed on Jun. 3, 2009, provisional application No. 61/183,792, filed on Jun. 3, 2009.

(51) Int. Cl.
*A61Q 11/00* (2006.01)
*A61K 31/69* (2006.01)
*A61Q 17/00* (2006.01)
*A61K 8/58* (2006.01)

(52) U.S. Cl.
CPC .............. *A61Q 11/00* (2013.01); *A61Q 17/005* (2013.01); *A61K 8/58* (2013.01); *A61K 31/69* (2013.01); *Y10S 514/835* (2013.01)
USPC ................. 424/49; 514/64; 514/835

(58) Field of Classification Search
USPC ...................... 514/64, 835; 424/49
See application file for complete search history.

(56) References Cited

U.S. PATENT DOCUMENTS

| | | | |
|---|---|---|---|
| 4,842,847 A | 6/1989 | Amjad | |
| 4,866,161 A | 9/1989 | Sikes et al. | |
| 4,894,220 A | 1/1990 | Nabi et al. | |
| 4,919,934 A | 4/1990 | Deckner et al. | |
| 5,288,480 A | 2/1994 | Gaffar et al. | |
| 5,605,676 A | 2/1997 | Gaffar et al. | |
| 7,390,806 B2 | 6/2008 | Lee et al. | |
| 2006/0217347 A1 | 9/2006 | Perry et al. | |
| 2007/0286822 A1 * | 12/2007 | Sanders et al. | 424/49 |

FOREIGN PATENT DOCUMENTS

| | | |
|---|---|---|
| EP | 0514417 | 11/1992 |
| RU | 2170079 | 7/2001 |
| RU | 2242965 | 12/2004 |
| WO | WO 2005/123094 | 12/2005 |
| WO | WO 2006/102604 | 9/2006 |

OTHER PUBLICATIONS

Gennaro, ed., 1995, *Remington: The Science and Practice of Pharmacy*, 19th ed., Easton, PA pp. 1399-1404.
Guggenheim et al., 2004, "Application of the Zürich biofilm model to problems of cariology," Caries Research 38(3):212-222.
Lindner, 1974, Emulsions and Emulsion Technology, Lissant ed., Dekker, pp. 188-190.
Merritt et al., 1984, "Diffusion Apparatus for Skin Penetration," J. Controlled Release I(2):161-162.
Sagarin et al., eds., 1972. "Emolient Materials," Cosmetics, Science and Technology, 2nd ed. vol. 1, pp. 32-43.
Wallhausser, 1974, "Antimicrobial Preservatives in Europe: Experience with Preservatives Used in Pharmaceuticals and Cosmetics," Develop. Biol. Standard 24:9-28.
Anonymous: "Amadol 5195: Lauramide DEA (Product datasheet)", Akzo Nobel Surface Chemistry, Feb. 6, 2004, XP002685162, Retrieved from the Internet: URL:http://doc.ccc-group/spec/953867.pdf.
Anonymous: "AmidexTM LSM Surfactant Product Specifications", Jun. 10, 2005, Retrieved from the Internet, Retrieved from: <http:1/www.lubrizol.com>, Retrieved on: Mar. 21, 2013.
Anonymous: "Testing Status of Agents at NTP CAS Registry No. 120-40-1" Retrieved from the Internet, Retrieved from: <http://ntp.niehs.nih.gov/>, Retrieved on: Mar. 21, 2013.
Isr & Written Opinion for International Application No. PCT/US2010/037220 mailed on Nov. 11, 2012.
Q. Luan et al.: "Inhibition of Experimental Periodontitis by a Topical Boron-based Antimicrobial" Journal of Dental Research, Feb. 2008, vol. 87, No. 2, pp. 148-152.

* cited by examiner

*Primary Examiner* — Kevin E Weddington
(74) *Attorney, Agent, or Firm* — Howard C. Lee (57) ABSTRACT

A stabilized oral care composition comprising a borinic acid derivative, e.g., a borinic ester.

18 Claims, 2 Drawing Sheets

BORINIC COMPOSITIONS

This application is a national stage entry under 35 U.S.C. §371 of International Patent Application No. PCT/US2010/0037220, filed Jun. 3, 2010, which claims the benefit of U.S. Provisional Application 61/183,788, filed Jun. 3, 2009 and U.S. Provisional Application 61/183,792, also filed Jun. 3, 2009, the contents of which are hereby incorporated herein by reference.

BACKGROUND OF THE INVENTION

The present invention relates to antimicrobial compositions containing a borinic acid derivative, e.g. a borinic ester. In particular embodiments, the invention covers oral compositions, for example dentifrice, for reducing bacteria in the mouth, e.g. for inhibiting and reducing plaque, gingivitis and dental caries.

Although some borinic esters are effective as antibacterial agents, incorporating borinic esters into oral care compositions presents difficulties, as borinic esters have proven to be unstable when added to aqueous compositions. For example, borinic esters may hydrolyze and decompose, e.g., in oral care compositions. Additionally, borinic esters may be insoluble in aqueous compositions. For example, the solubility of 3-hydroxypyridine-2-carbonyloxy-bis(3-chloro-4-methylphenyl)-borane in water is only 100 ppm, and its solubility in various oils may be less than 0.5%. There remains a need to develop compositions and methods to incorporate borinic acid derivatives stably in oral care compositions.

SUMMARY OF THE INVENTION

The present invention is directed to the surprising discovery that certain borinic esters are stable, soluble, and retain antimicrobial activity when incorporated into an oral care composition, e.g., a dentifrice or mouthwash.

In one embodiment, the borinic acid derivatives of the present invention are borinic esters, e.g. of formula A:

Formula A wherein $R_1$ and $R_2$ are the same or different (e.g. the same), and are selected from arylalkyl, aryl, cycloalkyl, or heterocycle (e.g. substituted or unsubstituted aryl or heteroaryl, for example phenyl, chlorophenyl, methylphenyl, or methylchlorophenyl); and $R_3$ is heteroaryl, heteroarylalkyl, heteroarylcarbonyl, or heteroarylalkylcarbonyl (e.g., substituted or unsubstituted heteroaryl, for example quinolinyl or hydroxypyridinylcarbonyl), in free or pharmaceutically acceptable salt form, in combination with a pharmaceutically acceptable carrier. For example, in one embodiment $R_1$ and $R_2$ are the same and are both aryl, e.g., phenyl, chlorophenyl, methylphenyl, or methylchlorophenyl.

Heteroaryl is for example an aryl group containing 1, 2 or 3 nitrogen atoms, for example pyridinyl, quinolinyl, hydroxypyridinyl, or hydroxyquinolinyl. Alkyl is for example $C_{1-4}$alkyl. Substitutions are for example halogen, e.g., chloro or fluoro, hydroxy, or $C_{1-4}$alkyl.

The borinic esters useful in the present invention thus include, for example, (i) boron picolinates, e.g. diaryl boron picolinates, for example 3-hydroxypyridine-2-carbonyloxy-bis(3-chloro-4-methylphenyl)-borane or 3-hydroxypyridine-2-carbonyloxy-bis(2-methyl-4-chlorophenyl)-borane, as well as (ii) diaryl borinic esters, for example diphenylborane-8-hydroxyquinolinate (PBHQ).

In one embodiment, the borinic esters are compounds as described in WO 2006/102604, incorporated herein by reference, e.g., of Formula (I)

Formula 1

(I)

wherein
$R^*$ and $R^{**}$ are independently substituted or unsubstituted aralkyl, substituted or unsubstituted aryl, substituted or unsubstituted cycloalkyl, or substituted or unsubstituted heterocycle;
z is 0 or 1, with the proviso, that if z is 1, then A is $CR^{10}$ or N, and D is N or $CR^{12}$, and with the further proviso that if z is O, then D is O, S or $NR^{12a}$;
E is hydrogen, hydroxy, alkoxy, (cycloalkyl)oxy, (cycloheteroalkyl)oxy, carboxy, or alkyloxycarbonyl;
m is 0 or 1;
$R^{12}$ is hydrogen, hydroxyalkyl, aminoalkyl, alkylaminoalkyl, dialkylaminoalkyl, carboxy, alkyloxycarbonyl, amido, hydroxy, alkoxy, aryloxy, thio, alkylthio, arylthio, alkylsulfonyl, dialkylaminosulfonyl, alkylaminosulfonyl, aminosulfonyl, sulfo, cyano, halo, nitro, amino, dialkylamino, alkylamino, arylamino, diarylamino, aralkylamino, or diaralkylamino;
$R^{12a}$ is hydrogen, substituted or unsubstituted alkyl, substituted or unsubstituted heteroalkyl, substituted or unsubstituted aralkyl, substituted or unsubstituted aryl, substituted or unsubstituted cycloalkyl, or substituted or unsubstituted heterocycle; and
$R^9$ and $R^{10}$ are independently hydrogen, alkyl, cycloalkyl, hydroxyalkyl, aminoalkyl, alkylaminoalkyl, dialkylaminoalkyl, halo, carbonyl, hydroxyimino, carboxy, alkyloxycarbonyl, alkylthio, alkylsulfonyl, arylthio, dialkylaminosulfonyl, alkylaminosulfonyl, aminosulfonyl, amino, alkoxy, nitro, sulfo, or hydroxy;
in free or pharmaceutically acceptable salt form.

"Aralkyl" and "alkaryl" are sometimes used to refer to arylalkyl and alkylaryl respectively. The alkyl or aryl portion of any moiety recited for $R^9$, $R^{10}$, or $R^{12}$ is optionally substituted, for example with hydroxy, halogen, or $C_{1-4}$ alkyl.

Alkyl is preferably $C_{1-4}$ alkyl. Cycloalkyl is preferably $C_{3-7}$ cycloalkyl. Aryl is preferably phenyl.

In some embodiments, E is a member selected from hydrogen, hydroxy, or (cycloheteroalkyl)oxy such as 2-morpholinoethoxy.

In other embodiments, $R^{12}$ is $(CH_2)_kOH$ (where k=1, 2 or 3), $CH_2NH_2$, $CH_2NH$-alkyl, $CH_2N(alkyl)_2$, $CO_2H$, $CO_2$alkyl, $CONH_2$, OH, alkoxy, aryloxy, SH, S-alkyl, S-aryl, $SO_2$alkyl, $SO_2N(alkyl)_2$, $SO_2NH$alkyl, $SO_2NH_2$, $SO_3H$, $SCF_3$, CN, halogen, $CF_3$, $NO_2$, $NH_2$, 2°-amino, 3°-amino, $NH_2SO_2$ or $CONH_2$.

In still other embodiments, $R^9$ and $R^{10}$ are independently hydrogen, alkyl, cycloalkyl, $(CH_2)_nOH$ (n=1 to 3), $CH_2NH_2$, $CH_2NH$alkyl, $CH_2N$(alkyl)$_2$, halogen, CHO, CH=NOH, $CO_2H$, $CO_2$-alkyl, S-alkyl, $SO_2$-alkyl, S-aryl, $SO_2N$(alkyl)$_2$, $SO_2NH$alkyl, $SO_2NH_2$, $NH_2$, alkoxy, $CF_3$, $SCF_3$, $NO_2$, $SO_3H$ or OH;

Compounds of Formula 1 may exist in rotameric form, and the illustrated dative bond (arrow) may or may not be present, i.e., the present invention includes those compounds in which coordination between the boron atom and the nitrogen or hydroxy of the picolinate is present and those compounds where such coordination is missing. The present invention also includes those compounds of Formula 1 in which a dative bond is formed between the boron and another atom of the molecule. In addition, those of skill in the art, e.g., organic and medicinal chemistry, will appreciate that the large difference in atomic radius between carbon and boron can allow for the formation of solvent coordination complexes in which a solvent molecule, such as water, can be inserted between the boron atom and the nitrogen atom of the picolinate ring. The present invention includes such adducts of the compounds of Formula 1.

In one embodiment of the invention in which z is 1, the compound of Formula 1 has a structure according to the following formula:

wherein D is selected from N and $CR^{12}$.

In another embodiment of the invention, in which z is 0, the compound of Formula 1 has a structure according to the following formula:

wherein D is a member selected from O, S and $NR^{12a}$.

In one embodiment of the invention, $R^*$ and $R^{**}$ are the same. In a more specific embodiment, $R^*$ and $R^{**}$ are substituted or unsubstituted aryl. In a still more specific embodiment, $R^*$ and $R^{**}$ are substituted or unsubstituted phenyl, wherein said substituted or unsubstituted phenyl has the structure:

and further wherein each of $R^4$-$R^8$ is a member independently selected from hydrogen, alkyl, cycloalkyl, aryl, substituted aryl, aralkyl, substituted aralkyl, hydroxyalkyl, aminoalkyl, alkylaminoalkyl, dialkylaminoalkyl, carboxy, alkylcarbonyl, aminocarbonyl, alkylaminocarbonyl, dialkylaminocarbonyl, hydroxy, alkoxy, aryloxy, thio, alkylthio, arylthio, alkylsulfonyl, diaminosulfonyl, alkylaminosulfonyl, aminosulfonyl, sulfo, cyano, halo, nitro, amino, 2°-amino, 3°-amino, aminosulfonyl, aminoalkyloxy, (alkylamino)alkyloxy, (dialkylamino)alkyloxy, and cycloheteroalkyl. Each alkyl or aryl portion of each moiety recited for $R^4$-$R^8$ is optionally substituted.

In more specific embodiments of the invention in which $R^*$ and $R^{**}$ are both optionally substituted phenyl as just described, each of $R^4$-$R^8$ is a member independently selected from the group consisting of: hydrogen, alkyl, cycloalkyl, aryl, substituted aryl, aralkyl, substituted aralkyl, $(CH_2)_kOH$ (where k=1, 2 or 3), $CH_2NH_2$, $CH_2NH$-alkyl, $CH_2N$(alkyl)$_2$, $CO_2H$, $CO_2$alkyl, $CONH_2$, $CONH$alkyl, $CON$(alkyl)$_2$, OH, alkoxy, aryloxy, SH, S-alkyl, S-aryl, $SO_2$alkyl, $SO_2N$(alkyl)$_2$, $SO_2NH$alkyl, $SO_2NH_2$, $SO_3H$, $SCF_3$, CN, halogen, $CF_3$, $NO_2$, $NH_2$, 2°-amino, 3°-amino, $NH_2SO_2$, $OCH_2CH_2NH_2$, $OCH_2CH_2NH$alkyl, $OCH_2CH_2N$(alkyl)$_2$, oxazolidin-2-yl, and alkyl substituted oxazolidin-2-yl.

In one embodiment of the invention in which $R^*$ and $R^{**}$ are both optionally substituted phenyl as described, $R^9$ is H, z is 1, A is CH, D is CH, E is OH, and m is O. In a more specific embodiment of the foregoing, $R^*$ and $R^{**}$ are both 3-chloro-4-methylphenyl. In another specific embodiment, $R^*$ and $R^{**}$ are both 2-methyl-4-chlorophenyl.

Particularly useful compounds include 3-hydroxypyridine-2-carbonyloxy-bis(3-chloro-4-methylphenyl)-borane and 3-hydroxypyridine-2-carbonyloxy-bis(2-methyl-4-chlorophenyl)-borane, in free or pharmaceutically acceptable salt form.

It has surprisingly been discovered that in formulations, the borinic ester compounds may exist in rotameric form, wherein the form is largely pH dependent, and the boron may be linked by a coordinate covalent bond (dative bond) to the nitrogen in the heteroaryl. The rotamer wherein the boron is nonpolar or associated with the hydroxy group on the picolinate moiety is predominantly or exclusively present at basic pH, while the more polar rotamer, wherein the boron is associated with the nitrogen on the picolinate or other heterocycle predominates at acidic pH. For example, High pH ---------------------------------------- Low pH It has also been discovered that the nonpolar rotamer or rotamer wherein the boron is associated with hydroxy is more stable in formulation. Without intending to be bound by theory, it is believed that the shift in electron density that occurs upon the formation of the dative bond with nitrogen makes the polar isomer more susceptible to hydrolysis at the ester bond.

To favor the more stable rotamer, we have discovered that it is advantageous that the pH of the formulation be maintained above 7, e.g., by using a buffer to prevent a drop in pH which would result in formation of the more polar rotamer, and/or that the pH be maintained even at a higher level, e.g., 8-9.5, it having been surprisingly shown that the compounds are stable at higher pH, and not (as might be suspected) highly vulnerable to degradation by OH⁻ ions. This discovery allows preparation of stable aqueous formulations of the compounds. We note that this discovery is somewhat in contrast to the examples of WO 2006/102604 which describe topical emulsions, with the borinic ester in the oil phase, or else compositions having relatively low pH, e.g., 5.5.

Thus, the invention provides Composition 1.0, a composition, e.g., an oral care composition, comprising an antibacterially effective amount of a borinic acid derivative, e.g., of Formula A, for example a compound of Formula (I), having a pH of at least 8, e.g. 8.5-11, for example about 9, or buffered to at least pH 7, and optionally further comprising one or more antioxidants, surfactants and solubilizing agents.

The present invention includes Composition 2.0, a dentifrice, comprising Composition 1.0 and a dentifrice vehicle, having a pH of at least 8, e.g. 8.5-11, for example about 9, or buffered to at least pH 7, and optionally further comprising one or more antioxidants, surfactants and/or solubilizing agents.

In another aspect, it has been discovered that borinic acid derivatives, e.g. of Formula A, which are often difficult to solubilize, are highly soluble in polymers comprising polyoxyethylene or polyoxyethylene and polyoxypropylene. Thus in another embodiment the present invention comprises Composition 3.0, an oral care composition, e.g., according to any of Compositions 1.0 to 2.0, comprising borinic acid derivatives, e.g. of Formula A, for example a Compound of Formula I, and a solubilizing agent, e.g., selected from polymers of polyoxyethylene and polyoxyethylene/polyoxypropylene.

It has also been found that buffering the formulation enhances stability. The invention thus provide provides Composition 4.0, an oral care formulation comprising an antibacterially effective amount of a borinic acid derivative, e.g., of Formula A, for example a compound of Formula (I), for example any of Compositions 1.0 et seq.-3.0 et seq. more fully described below, in combination with a suitable buffer, for example a phosphate buffer.

The present invention also includes Method 5.0, a method for preparing an oral care composition comprising mixing any of Compositions 1.0-4.0 with an orally acceptable vehicle and adjusting or maintaining the pH at a level of at least 7, preferably at least 8, e.g., 8.5-11.

The present invention also includes Method 6.0, a method to reduce, inhibit, or treat oral microbial infections, for example to reduce or inhibit formation of dental caries, to treat, reduce or inhibit gingivitis, to reduce levels of oral bacteria, to inhibit microbial biofilm formation in the oral cavity, to reduce plaque accumulation, and/or clean the teeth and oral cavity, comprising applying a Composition of the Invention to the oral cavity of a subject in need thereof.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The oral compositions of the present invention may include a dentifrice, mouth rinse, dental floss, dental paint, dental film, lozenge, or confectionary. Dentifrice compositions may include a toothpaste, gel, or powder.

"Orally acceptable salts" are pharmaceutically acceptable acid or base addition salts that are safe for use in an oral care product such as a dentifrice in the amounts and concentrations provided by normal use of the product.

Compounds of Formula (I) which may be useful in the present invention include: 3-hydroxypyridine-2-carbonyloxy-bis(3-chloro-4-methylphenyl)-borane (or bis(3-chloro-4-methylphenyl)borinic acid 3-hydroxypicolinate ester), e.g. of Formula (II):

Thus, in one aspect of the present invention, Composition 1, e.g., a composition, e.g., an oral care composition, comprising an antibacterially effective amount of a borinic acid derivative, e.g., of Formula A, for example a compound of Formula (I), having a pH of at least 7, preferably at least 8, e.g. 8.5-11, for example about 9, and optionally further comprising one or more antioxidants, surfactants and solubilizing agents, includes, for example, any of the following compositions:

1.1 Composition 1 comprising a borinic ester.
1.2 Composition 1.1 comprising a borinic ester of Formula 1.
1.3 Composition 1.1 or 1.2 comprising a diaryl boron picolinate.
1.4 Composition 1.1, 1.2 or 1.3 comprising 3-hydroxypyridine-2-carbonyloxy-bis(3-chloro-4-methylphenyl)-borane or 3-hydroxypyridine-2-carbonyloxy-bis(2-methyl-4-chlorophenyl)-borane.
1.5 Composition 1.4 comprising 3-hydroxypyridine-2-carbonyloxy-bis(3-chloro-4-methylphenyl)-borane.
1.6 Composition 1 comprising a diaryl borinic ester.
1.7 Composition 1.6 wherein the diaryl borinic ester is diphenylborane-8-hydroxyquinolinate (PBHQ).
1.8 Any of compositions 1.0-1.7, wherein the compound of formula (A) is present in an amount of 0.05% to 20% by weight, e.g., 0.1% to 10%.
1.9 Any of compositions 1-1.8 comprising buffering agents to raise and maintain the pH at the desired level.
1.10 Composition 1.9 wherein the buffering agent includes a basic amino acid in free or pharmaceutically acceptable salt form
1.11 Composition 1.10 wherein the basic amino acid is selected from arginine, lysine, citrullene, ornithine, creatine, histidine, diaminobutanoic acid, diaminoproprionic acid and mixtures thereof, in free or pharmaceutically acceptable salt form.

1.12 Composition 1.12 wherein the basic amino acid is arginine in free or pharmaceutically acceptable salt form.

Without intending to be bound by theory, it is believed that compounds of Formula A, e.g., the borinic esters of Formula (I) may be oxidized by oxygen, peroxides, or by peroxides that can be formed in oral compositions, e.g., from ethers such as polyethylene glycol reacting with oxygen. Such oxygen and/or peroxides may react with the borinic ester at the carbon-boron bond, leading to cleavage and formation of boronic acid derivatives and phenol derivatives, which are ineffective antibacterial agents. It is believed that the addition of antioxidants reduces the peroxides and other oxidizing agents that may be present or form in the oral compositions.

Thus, in one aspect of the present invention, Composition 1.0 thus includes for example, any of the following compositions:

1.13 Any of Compositions 1.0-1.8 further comprising an antioxidant.
1.14 Composition 1.9 wherein the antioxidant is selected from ascorbic acid, sodium ascorbyl phosphate, butylated hydroxytoluene (BHT), alpha tocopherol, citric acid, and a mixture thereof.
1.15 Any of Compositions 1.9-1.10 wherein the antioxidant is present in an amount sufficient to inhibit oxidation of the borinic acid derivative;
1.16 Any of compositions 1.9-1.11 wherein the antioxidant is present in an effective amount to prevent or inhibit oxidation of the compound of formula (I).

In one embodiment of the present invention, the compounds of formula (I) are solubilized in the compositions of the present invention with a solubilizing agent, which may include for example polyethylene glycol, glycerin, co-polymers of polyethylene glycol and polypropylene glycol (e.g., Pluraflo L4370), or Triblock Copolymer Surfactant F127. The amounts of solubilizing agent required will be dependent upon the amount of the compounds of Formula (I) in the composition, and the particular solubilizing agent selected. Thus, the present invention includes the following compositions:

1.17 Any of compositions 1.0-1.12 further comprising a solubilizing agent.
1.18 Composition 1.13 wherein the solubilizing agent is a nonionic surfactant.
1.19 Composition 1.14 wherein the solubilizing agent comprises an alkyl ether, for example a polyalkyleneglycol, for example polyethylene glycol, polypropylene glycol, or co-polymers or mixtures of any of these.
1.20 Any of compositions 1.13-1.15 wherein the compound of Formula A is solubilized in the solubilizing agent prior to mixture with the other composition ingredients.
1.21 Any of compositions 1.13-1.16 wherein the solubilizing agent is present in an amount of from 1-30% by weight, for example 5-10% by weight.

The compositions of the invention also may optionally include one or more chelating agents which are able to complex calcium found in the cell walls of the bacteria, which, it is believed weakens the bacterial cell wall and augments bacterial lysis. Chelating agents may further sequester ions that could complex with and destabilize the borinic acid derivatives. Agents suitable for use as chelating agents are known to those of skill in the art, and include di- or tetra-acids and their salts, such as the soluble pyrophosphates, polycarboxylic acids, and polyaminocarboxylic acids. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1 wt. % pyrophosphate ions, about 1.5 wt. % to about 6 wt. %, about 3.5 wt. % to about 6 wt. % of such ions. Useful chelating agents include tetrasodium pyrophosphate, tetrapotassium pyrophosphate, ethylene diamine tetraaceticacid, ethylene glycol tetraacetic acid, sodium pyrophosphate, sodium tripolyphosphate, potassium tripolyphosphate, sodium hexametaphosphate, and citric acid. Accordingly, in a further embodiment, the invention provides 1.22 Any of compositions 1.0-1.17 further comprising a chelator.
1.23 Composition 1.22 wherein the chelator is selected from tetrasodium pyrophosphate, tetrapotassium pyrophosphate, ethylene diamine tetraaceticacid, ethylene glycol tetraacetic acid, sodium pyrophosphate, sodium tripolyphosphate, potassium tripolyphosphate, sodium hexametaphosphate, and citric acid.
1.24 Any of compositions 1.22 or 1.23 wherein the chelator provides ion in an amount by weight of 1-6%

In one embodiment, Composition 2.0 of the present invention is an oral care product, comprising an effective amount of Composition 1.0 and an orally acceptable carrier. Acceptable carriers suitable for use in an oral care product are known by those of skill in the art, and may take the form of a paste, gel or mouthwash which includes water and/or a humectant, or may take the form of a powder, or a dental floss or dental device. The components of the acceptable carrier may include Composition 1.0. Humectants are known by those of skill in the art, and include edible polyhydric alcohols such as glycerine, sorbitol, xylitol, alkylene glycol such as polyethylene glycol or propylene glycol as well as other polyols and mixtures of these humectants. The oral compositions of the present invention may comprise from about 5% to about 80% by weight of the humectant, with water and other components making up the balance of the carrier.

2.1 Composition 2 in the form of a paste, gel or liquid comprising any of compositions 1-1.24 in combination or association with water and/or a humectant.
2.2 Composition 2.1 wherein the amount of water is less than 10%.
2.3 Composition 2.1 or 2.2 wherein the amount of humectant is greater than 50%.
2.4 Any of Compositions 2-2.3 wherein the humectant is selected from polyhydric alcohols (e.g. glycerine, sorbitol, xylitol) and alkylene glycol (polyethylene glycol or propylene glycol as well as other polyols and mixtures.
2.5. Any of Compositions 2-2.4 which is a dentifrice.
2.6 Composition 2.5 which is a toothpaste.
2.7 Composition 2.5 or 2.6 which further comprises an abrasive.
2.8 Composition 2.7 which further comprises a fluoride ion source.

In another embodiment, the invention provides an oral care composition, Composition 3.0, e.g., according to Composition 1.0 through 2.8, comprising borinic acid derivatives, e.g. of Formula A, for example a compound of Formula I, and at least one solubilizing agent selected from polymers of polyoxyethylene and/or polyoxypropylene, e.g.

3.1 Composition 3.0 wherein the solubilizing agent comprises a co-polymer of polyethylene glycol and polypropylene glycol, e.g., Fluraflo L4370 (BASF).

3.2 Composition 3.0 wherein the solubilizing agent comprises a poloxamer, e.g. a tri-block co-polymer of formula H—(O—CH$_2$—CH$_2$)$_x$—(O—CH(CH$_3$)CH$_2$)$_y$—(O—CH$_2$—CH$_2$)$_z$—OH.

3.3 Composition 3.2 wherein the average molecular weight of the polyoxypropylene block in the poloxamer is approximately 3-4 kD, the polyoxyethylene content is approximately 65-75%, and the total average molecular weight of the poloxamer is approximately 12-13 kD, for example wherein x and z are each 90-110, e.g about 101, and y is 50-65, e.g., about 56, for example wherein the poloxamer is poloxamer 407 (e.g., Pluronic® F-127 from BASF).

3.3 Composition 3.0 wherein the solubilizing agent comprises polyethylene glycol, e.g. having an average molecular weight of 100 to 1000 daltons, for example, e.g., PEG 300 or PEG 600.

3.4 Composition 3.0 wherein the solubilizing agent comprises an agent selected from co-polymers of polyethylene glycol and polypropylene glycol, polaxamers, polyethylene glycols, and mixtures thereof.

It has also been discovered that the stability of the borinic acid derivatives is significantly enhanced by use of buffering agents, even to a large extent at neutral pH. The invention provides in a further embodiment Composition 4, an oral care formulation, e.g., according to any of the preceding Compositions 1.0 through 3.4, comprising an antibacterially effective amount of a borinic acid derivative, e.g., of Formula A, for example a compound of Formula (I), and a buffer, having a pH of about 7 to about 11, for example a pH of at e.g., at least 8, for example having a phosphate buffer providing a pH of at least 7.2.

The oral care compositions of the present invention may also contain one or more fluoride ion sources, e.g., fluoride salts which may be soluble. Fluoride salts wherein the fluoride is covalently bound to another atom and/or sequestered from calcium are preferred. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000-about 1600 ppm, e.g., about 1450 ppm.

Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

The oral compositions of the present invention may also comprise an additional antibacterial agent, which are know by those of skill in the art, such as a halogenated diphenyl ether (triclosan), herbal extracts or essential oils, bisguanide antiseptics, phenolic antiseptics, hexetidine, povidone iodine, delmopinol, salifluor, metal ions (e.g., zinc salts, for example, zinc citrate), sanguinarine, and propolis.

The oral compositions of the present invention may also comprise a tooth desensitizing agent, which are known by those of skill in the art, and include a potassium salt, capsaicin, eugenol, a strontium salt, a zinc salt, a chloride salt, or combinations thereof.

The oral compositions of the present invention may comprise abrasives and/or polishing agents, such as calcium and silica abrasives, which are known by those of skill in the art. Preferred calcium abrasives may include a calcium phosphate abrasive, e.g., tricalcium phosphate (Ca$_3$(PO$_4$)$_2$), hydroxyapatite (Ca$_{10}$(PO$_4$)$_6$(OH)$_2$), or dicalcium phosphate dihydrate (CaHPO$_4$.2H$_2$O). Useful silica abrasives may include precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size of about 0.1 and about 30 microns, about 5 and about 15 microns. The silica abrasives can be from precipitated silica or silica gels, such as the silica xerogels, which may be are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119.

In certain embodiments, abrasive materials useful in the practice of the oral care compositions in accordance with the invention include silica gels and precipitated amorphous silica having an oil absorption value of about less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns.

In particular embodiments, the abrasive materials comprise very small particles, e.g., having a d50 less than about 5 microns. For example small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3-about 8% SPS and about 25-about 45% of a conventional abrasive.

It has been found that oral compositions containing silica and the compounds of Formula (I) change color, from white to yellow, which is undesirable. Such a color change is observable even if the composition contains antioxidants (previously discussed). The present invention is also based on the surprising discovery that the addition of a chelating agent to the oral composition can inhibit such color change, indeed, reverse such color change. Chelating agents useful to prevent such color change have been previously discussed.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

The oral care compositions of the invention also may include an agent to increase the amount of foam that is produced when the oral cavity is brushed, and such agents are known by those of skill in the art. Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

The oral compositions of the present invention may also a surfactant or a mixture of compatible surfactants, which are known by those of skill in the art. Suitable surfactants are those which are reasonably stable throughout a wide pH range, for example, anionic, cationic, nonionic or zwitterionic surfactants, including mixtures thereof.

Anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms, e.g., sodium lauryl sulfate, sodium lauroyl sarcosinate and sodium coconut monoglyceride sulfonates. Mixtures of anionic surfactants may also be utilized.

Cationic surfactants useful herein may include derivatives of aliphatic quaternary ammonium compounds having one long alkyl chain containing about 8 to about 18 carbon atoms, e.g., lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, and cetyl pyridinium fluoride.

Nonionic surfactants that can be used in the compositions of the invention can be defined as compounds produced by the condensation of alkylene oxide groups (hydrophilic in nature) with an organic hydrophobic compound which may be aliphatic or alkylaromatic in nature. Examples of nonionic surfactants useful in the present invention include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Polaxamers are a particular type of nonionic surfactant that can be used in the invention. Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade name Pluronics. Because the lengths of the polymer blocks can be customized, many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic tradename, coding of these copolymers starts with a letter to define its physical form at room temperature (L=liquid, P=paste, F=flake (solid)) followed by two or three digits, The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61.

Zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

The oral care compositions of the invention may also include one or more flavoring agents, which are known by those of skill in the art. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, rosemary, eucalyptus, marjoram, cinnamon, lemon, lime, grapefruit, and orange. Also useful are such chemicals as menthol, carvone, and anethole, and other extracts, such as green tea extract.

The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to about 0.05% by weight and in another embodiment about 0.005 to about 0.015% by weight.

The oral care compositions of the invention also optionally include one or more polymers, which are known by those of skill in the art, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include about 1:4 to about 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139(M.W. 500,000), AN 119 (M.W. 250,000) and S-97 Pharmaceutical Grade (M.W. 70,000), of GAF Chemicals Corporation. Such copolymers may improve the antibacterial activity of the compounds of Formula (I) (IR8387).

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. Such thickening materials are known by those of skill in the art, and may include carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

The oral care compositions of the invention may also optionally include one or more enzymes known by those of skill in the art. Useful enzymes include proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. An enzyme of a mixture of several compatible enzymes in the current invention constitutes about 0.002% to about 2% in one embodiment or about 0.05% to about 1.5% in another embodiment or in yet another embodiment about 0.1% to about 0.5%.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents, which are known by those of skill in the art.

The compositions of the present invention can be made using methods which are common in the oral product area.

The present invention in one method aspect involves applying to the oral cavity a safe and effective amount of the oral care compositions described herein, e.g. with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) reduce dry mouth, (xiii) clean the teeth and oral cavity (xiv) reduce erosion, (xv) whiten teeth, and/or (xvi) kill or inhibit cariogenic bacteria.

The oral compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wal interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w))$_5$ then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into oral care formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some borinic acid complexes in water is less than 0.00025% wt/wt. The solubility of the same borinic acid complexes can be less than about 2% wt/wt in either propylene glycol or isopropyl myristate. In one embodiment of the present invention, diethylene glycol monoethyl ether (DGME) is the solvent used to dissolve the compounds of Formula I. The borinic acid complexes useful in the present formulation are believed to have a solubility of from about 10% wt/wt to about 25% wt/wt in DGME. In another embodiment a DGME water cosolvent system is used to dissolve the compounds of Formula I. The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt. This increased solubility reduces the likelihood of reduced bioavailability caused by precipitation.

Liquid forms may include a suitable aqueous or nonaqueous vehicle with buffers, suspending and dispensing agents, thickeners, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like. Additionally, the compounds can be delivered using a sustained-release system, such as semipermeable matrices of solid hydrophobic polymers containing the therapeutic agent. Various sustained-release materials have been established and are well known by those skilled in the art.

The invention is further described in the following examples. The examples are merely illustrative and do not in any way limit the scope of the invention as described and claimed

EXAMPLE 1

Stability in Low Water Dentifrice

The stability of a dentifrice formulation containing the active ingredient, 3-hydroxypyridine-2-carbonyloxy-bis(3-chloro-4-methylphenyl)-borane (COMPOUND 1), in a silica base is evaluated at different water levels. The formulations are as follows:

TABLE 1

| Component (% w/w) | 0% added water | 6% added water | G series |
|---|---|---|---|
| Demineralized water | | 6.0 | 31.367 |
| 99.0-101.0% vegetable | 69.507 | 53.407 | 30.84 |

TABLE 1-continued

| Component (% w/w) | 0% added water | 6% added water | G series |
|---|---|---|---|
| glycerin | | | |
| Dental type Silica - Zeodent 105 - high cleaning silica | | 12 | 10 |
| Dental type silica abrasive (Zeodent 115) | | | 8.5 |
| Dental type silica - Zeodent 114-synth. amorphous ppt silica | 8 | 12 | |
| Dental type silica - Zeodent 165-synth. amorphous ppt silica | 9 | | 2.5 |
| Tetrasodium pyrophosphate - fine | 0.5 | 0.5 | 0.5 |
| Sodium saccharin | | 0.3 | 0.3 |
| COP Sodium saccharin | 0.3 | | |
| Sodium fluoride | 0.243 | 0.243 | 0.243 |
| Sucralose | 0.15 | 0.15 | 0.15 |
| Titanium dioxide | 1 | 0.75 | 0.75 |
| Carrageenan concentrate PS-223 | 0.4 | | |
| Sodium CMC-12 | | | 1 |
| Sodium CMC food grade 7MF | 0.4 | | |
| Poly(vinylpyrrolidone)(Polyclar ® 10) | | 1 | |
| Xanthan gum | | 0.3 | 0.5 |
| Gantrez S-97 | | 1.95 | 1.95 |
| Sodium hydroxide 50% solution | | 1.2 | 1.2 |
| Flavor K91-6507 | 1.3 | 1 | 1 |
| Polyethylene glycol 300 | 6.25 | 6.72 | 6.72 |
| Compound 1 | 0.75 | 0.75 | 0.75 |
| Sodium Lauryl Sulfate powder | 1.7 | 1.5 | 1.5 |
| Sodium ascorbyl phosphate | | 0.2 | 0.2 |
| Butylated hydroxytoluene | | 0.03 | 0.03 |
| Vitamin E | 0.5 | | |

Incorporating Compound 1 into low-water dentifrice enhances the stability of the active ingredient in comparison to dentifrice formulas with higher water content. These low water formula options exhibit antibacterial and anti-inflammatory efficacy in-vitro equivalent to a positive control, Colgate Total® with triclosan as antibacterial agent.

The difference in water levels among these formulations is significant. The G series has a water activity level (expressed as vapor pressure of water in sample over vapor pressure of free water at the same temperature) of 0.75, compared to 0.25 for the 6% water formulation, and 0.09 for the formulation with no added water. The stability of Compound 1 over time in the different formulations is shown in the following table:

TABLE 2

| | Initial | | 1 month CRT | | 1 month 40° C. | | 2 month CRT | | 2 month 40° C. | |
|---|---|---|---|---|---|---|---|---|---|---|
| | Cp 1 | F⁻ | Cp 1 | F⁻ | Cp 1 | F⁻ | Cp 1 | F⁻ | Cp 1 | F⁻ |
| 6% added water | 0.72 (96%) | 1153 ppm | 0.71 (94%) | 1077 ppm | 0.70 (93%) | 1160 ppm | 0.74 (99%) | 1215 ppm | 0.68 (91%) | 1041 ppm |
| 0% added water | 0.67 (90%) | 1042 ppm | 0.72 (96%) | 1131 ppm | 0.68 (91%) | 1130 ppm | 0.72 (96%) | 1160 ppm | 0.61 (81%) | 1135 ppm |
| G-series | 0.72 (96%) | 1144 ppm | 0.74 (99%) | 1026 ppm | 0.66 (93%) | 1076 ppm | 0.71 (99%) | 880 ppm | 0.51 (91%) | 990 ppm |

The reduction in the water level in the dentifrice appears to have a positive impact on the stability of Compound 1 in the formulation. After two months aging at controlled room temperature and 40° C., there is less drop in the % recovery of Compound 1 in the 0% and 6% added water formulations than in the more conventional G-series formulation.

The stability of these formulations is also challenged by the addition of a 1:1 molar ratio of hydrogen peroxide to Compound 1. Formulations which are susceptible to degradation by hydrogen peroxide are less stable upon aging. For example, the G-series formula had a 59% Compound 1 recovery after three months at 40° C. and 35% recovery of Compound 1 after peroxide challenge while a more stable formula, used as a positive control in this experiment, exhibited 87% recovery after three months 40° C. and 85% recovery after challenge with peroxide. (Note: The positive control for this experiment was chemically stable but ineffective in in-vitro test). There is only a 1% drop in Compound 1 recovery in the 0% added water formulation and a 10% drop in % recovery in the 6% added water formulation. Both formulations demonstrate significantly less degradation than the 44% drop in Compound 1 recovery observed in the G-series formula.

Based on the peroxide challenge experiment and the two months aging results, it can be concluded that reducing the level of water in the dentifrice enhances the stability of the active. The 0% and 6% added water formulations are tested in an assay measuring inhibition of growth of A. viscosus and shown to retain their antibacterial efficacy. The 0% added water formulation is also tested in an anti-inflammatory assay measuring induction of PGE2 and shown to be as effective as the positive control, Total® toothpaste with triclosan, with a value of <200 pg/ml PGE2 vs>1200 pg/ml for placebo control, and about 400 pg/ml for the G formulation.

EXAMPLE 2

High pH Formulations

The stability of a dentifrice formulation containing the active ingredient, 3-hydroxypyridine-2-carbonyloxy-bis(3-chloro-4-methylphenyl)-borane (COMPOUND 1), in a silica base is evaluated at different water levels. It is found that the stability of COMPOUND 1 in dentifrice is dependent on the pH of the formula. Specifically, a significant increase in stability is observed when the pH of the dentifrice is increased from 7 to 9, without negative impact on the antibacterial or anti-inflammatory efficacy of the formulation.

The first formula base is referred to as the G-series and the second referred to as the low water formula, corresponding to the G-series and 6% added water formulations of the preceding example. The major difference between the two formulas is the level of added water. The G-series has about 32% added water while the low water formula has 6% added water. In both formulations the level of COMPOUND 1 is 0.75%. The pH is varied by adjusting the ratio of sodium hydroxide to glycerin in the formulations of the previous example to obtain dentifrices at pH 7, 8.5 and 9.

The results of COMPOUND 1 stability upon accelerated aging at 40° C. is shown in Table 2. For the G-series, the percentage of COMPOUND 1 recovery after three months of accelerated aging is nearly 30% greater in the pH 8.5 and pH 9 formulas when compared to the formula at pH 7. The same trend is also observed in the low water formula. These results demonstrate a marked improvement in COMPOUND 1 stability as a result of increasing the dentifrice pH. Although the pH is the major driver, the reduction in the water level also appears to have a positive impact on the stability of COMPOUND 1 in the formula.

After two months aging at controlled room temperature and 40° C. there is less drop in the % recovery of COMPOUND 1 in the 0% and 6% added water formulas than in the G-series formula:

TABLE 3

% COMPOUND 1 recovery after accelerated aging at 40° C.

| | Initial | 1 Month | 2 Month | 3 Month |
|---|---|---|---|---|
| G - pH 7 | 90% | 88% | 68% | 61% |
| G - pH 8.5 | 108% | 104% | 96% | 89% |
| G - pH 9 | 100% | 97% | 97% | 90% |
| LW - pH 7 | 99% | 93% | 87% | 63% |
| LW - pH 8.5 | 103% | 100% | 96% | 100% |
| LW - pH 9 | 97% | 97% | 92% | 97% |

To further investigate the effect of pH on COMPOUND 1 stability, a series of pastes are prepared having pH values ranging from 5.7 to 9. The pastes are aged at 60° C. for two weeks in order to quickly evaluate trends in formula stability as a function of pH. In the G-series, the percentage of COMPOUND 1 recovered decreases as the pH decreases from pH 9 to pH 7.5 but increases from pH 7 to pH 5.7. In the low water base, the percentage of COMPOUND 1 recovered decreases from pH 9 to pH 5.7. While the stability at acidic pH is different in the two formula bases, pH 9 results in the greatest percentage COMPOUND 1 recovery in both formulas. In addition, it was observed that the ratio of COMPOUND 1 isomers strongly depends on pH. At pH 9, COMPOUND 1 exists only in its nonpolar form and the amount of the polar rotamer increases as pH of the dentifrice decreases. A similar trend is observed in the liquid dentifrice.

Figure 1:
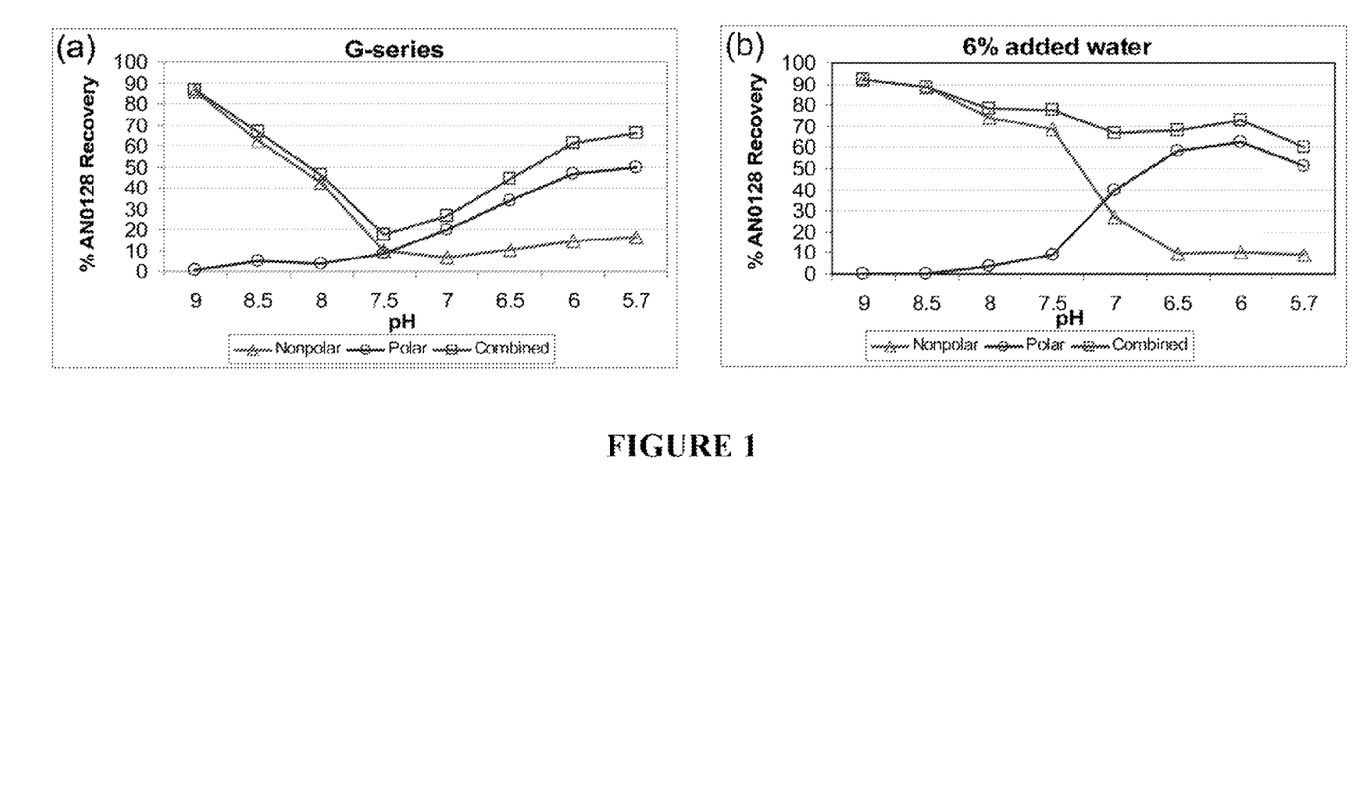
FIG. 1 depicts percent of COMPOUND 1 recovery after two weeks at 60° C. as a function of formula pH in the (a) G-series base and (b) the low water base, as further described in the examples.

FIG. 1 shows the percentage of COMPOUND 1 recovery after two weeks at 60° C. as a function of formula pH in the (a) G-series base and (b) the low water base.

Figure 2:
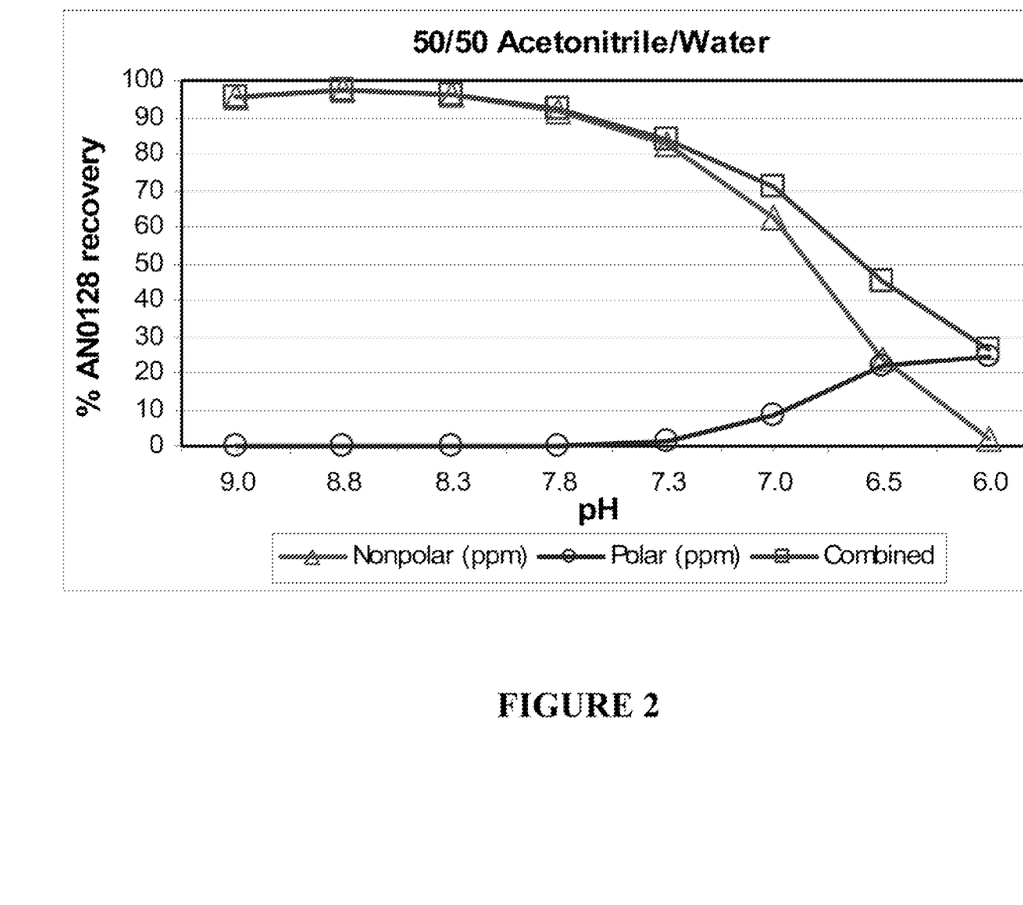
FIG. 2 shows the percentage of COMPOUND 1 recovery in a 50/50 acetonitrile/water solution as a function of pH after 1 day at 70° C., as further described in the examples.

As dentifrice contains many components, it is important to understand whether the observed relation between COMPOUND 1 stability and pH is dependent on a dentifrice ingredient or is simply the response of COMPOUND 1 to pH itself. Therefore, a study of the effect of pH on COMPOUND 1 is conducted in a simple solution of 50/50 acetonitrile/water. The result is shown in FIG. 2. In this study, a series of samples having pH from 9 to 6 were prepared and aged at 70° C. for one day. The solution at pH 9 had the highest percentage of COMPOUND 1 recovery. It was also observed that only the nonpolar isomer is present at pH 9 and the ratio of the nonpolar to polar rotamer decreases as the pH decreases, the same trend observed in dentifrice. These results indicate that the nonpolar rotamer of COMPOUND 1 is fundamentally less susceptible to degradation and the ratio of nonpolar to polar isomer is directly affected by pH. These results help to explain the observed increase in % COMPOUND 1 recovery in formulas at pH 9 and 8.5 compared to pH 7. Differences between the stability of COMPOUND 1 at lower pH in the two formula bases likely reflect the ability of formula ingredients to partially stabilize the polar rotamer.

FIG. 2 shows the percentage of COMPOUND 1 recovery in a 50/50 acetonitrile/water solution as a function of pH after 1 day at 70° C.

The anti-inflammatory effect of COMPOUND 1 does not appear to have been impacted by an increase in dentifrice pH. Both the G-series and low water formulas at pH 7 and 9 performed well in the suppression of the anti-inflammatory marker PGE2. The antibacterial effect of COMPOUND 1, as measured by growth inhibition of *A. viscosus*, is comparable to that of the pH 7 paste as well as commercial high quality toothpaste.

The uptake of COMPOUND 1 onto the hydroxyapatite (HAP) disk is significantly increased by the increase in pH. Although the release of COMPOUND 1 at pH 9 is only 29%, the quantity of COMPOUND 1 released by G-pH 7 and G-pH 9 formulas is equivalent.

EXAMPLE 3

Efficacy of Compound 1 in Inhibiting Oral Bacteria

The minimum inhibitory concentration for COMPOUND 1 against common oral bacteria is found to be as follows. Ethanol is used as vehicle.

TABLE 4

| | Bacterial Species | ppm |
|---|---|---|
| Gram Negative | A. actinomycetemcomitans | >15.6 |
| | F. nucleatum | 1-2 |
| | P. gingivalis | ≤0.12 |
| | P. intermedia | 3.9-7.8 |
| | T. forsythia | |
| | T. denticola | |
| | V. parvula | 7.8 |
| Gram Positive | A. naeslundii | 1-2 |
| | A. viscosus | 1 |
| | E. nodatum | |
| | L. casei | 2-3.9 |
| | S. gordonii | ≤0.12-0.25 |
| | S. mutans | 0.25-0.5 |
| | S. oralis | ≤0.12-0.25 |
| | S. sanguinis | 0.25-0.5 |
| | S. sobrinus | ≤0.12-0.5 |

EXAMPLE 4

Solubilization of Compound 1 a. Solubilization in Copolymers of Ethylene Glycol and Propylene Glycol

The poor solubility of Compound A presents some formulation challenges. Its solubility in water is less than 100 ppm, and its solubility in flavor oils (often used to solubilize actives) is less than 0.5%. We have discovered that co-polymers of polyethylene glycol and polypropylene glycol are able to solubilize Compound 1. Fluraflo L4370 (BASF) is able to solubilize 1% Compound 1 (% w/w). It is necessary to stir the solution over low heat to fully solubilize the active. The resulting solution is cloudy, reflecting the nature of the Fluraflo L4370 itself. The solution of 1% Compound 1 in Fluraflo L4370 is diluted 1:1 with 1.5% SLS in water to produce a clear solution, composed of 0.5% AN0128, 0.75% SLS, 50% Fluraflo L4370 in water Similar results are achieved using Fluracare L1220.

The solution of 0.5% AN0128.0.75% SLS. 50% Fluraflo L4370 in water is then tested in a biofilm disruption assay. The percent reduction achieved versus the negative control is 65%, indicating that Compound 1 retains its antibacterial activity when solubilized in Fluraflo L4370.

b. Solubilization Using Tri-Block Co-Polymer

We also discovered that Tri-block Co-polymer Surfactant F127 is able to further enhance solubilization of Compound 1. In experimental liquid dentifrice formulas (Table 3), Compound 1 is not completely soluble over time, as evidenced by precipitation and crystallization over time. After the addition of 5% F127, experimental liquid dentifrice formulas (Table 4) remain clear. Therefore, Tri-block Co-polymer Surfactant F127 is able to further solubilize Compound 1 and is suitable for use in formulations.

TABLE 5

Experimental formulations without tri-block co-polymer

| | A2 | A3 |
|---|---|---|
| Compound 1 | 0.6 | 0.6 |
| PEG-300 | 12 | 12 |
| Propylene glycol | 10 | 10 |
| Fluroflo L4370 | 10 | 10 |
| Glycerin | | 10 |
| SLS | 1.5 | 1.5 |
| $H_2O$ | 38 | 38 |
| Total | 72.1 | 72.1 |

TABLE 6

Experimental formulations with tri-block co-polymer

| | A5 | A6 |
|---|---|---|
| Compound 1 | 0.6 | 0.6 |
| PEG-300 | 11.4 | 11.4 |
| Propylene glycol | 10 | 10 |
| Fluroflo L4370 | 10 | 10 |
| Glycerin | | 10 |
| SLS | 1.5 | 1.5 |
| $H_2O$ | 34 | 34 |
| Pluronic F127 | 5 | 5 |
| Total | 72.5 | 72.5 | c. Solubilization Using PEG

We further discovered that low molecular weight polyethylene glycol 300 (PEG 300)(Dow Chemical Company) solubilizes 10% Compound 1 (% w/w). It is necessary to stir the solution over low heat to fully solubilize the active. The resulting solution is clear with a slight yellow tint due to the color of Compound 1. We also discovered that PEG 600 can solubilize Compound 1. Therefore, we conclude that solvents containing oligomers and/or polymers of ethylene glycol are capable of solubilizing Compound 1 and are suitable for formulation.

A solution of 2% Compound 1 in PEG 300 is diluted 1:1 with 2% SLS in water to produce a solution composed of 1% Compound 1, 1% SLS, 50% PEG 300 in water which is then tested in a biofilm disruption assay. The percent reduction achieved versus the negative control is 76%, indicating that Compound 1 retains its antibacterial activity when solubilized in PEG 300.

The properties of Compound 1 in conjunction with other excipients are further evaluated by diluting a solution of Compound 1 in PEG 300 into other solvents such as propylene glycol and glycerin at varying ratios. A solution containing 1% Compound 1 in 19% PEG 300 and 80% propylene glycol is clear. This solution is then diluted 1:1 with 1% SLS in water to produce a solution composed of 0.5% Compound 1, 0.5% SLS, 9.5% PEG 300 and 40% propylene glycol in water which is then tested in the biofilm disruption assay. The percent reduction achieved versus the negative control is 80%. These results indicate that Compound 1 retains its antibacterial activity in the mixed solvent solution. Similar results are achieved with PEG and glycerin.

EXAMPLE 5

Buffered Formulations

Two pH 7.2 formulations of Compound 1 are prepared, one with phosphate buffer, one without, and the decomposition of Compound 1 is measured over 14 days. While measurable decomposition is seen in both formulations, the slope of the rate of decomposition Compound 1 in the buffered formulation is decreased by 3.3 fold compared to that of the unbuffered formulation.

EXAMPLE 6

Effect of Gantrez

Addition of Gantrez into liquid formulations of Compound 1 is shown to improve the activity of the compound in a biofilm assay. Compositions are prepared as follows:

TABLE 7

| Liquid dentifrice ID | G5 | G7 |
|---|---|---|
| Compound 1 | 0.5 | 0.5 |
| BHT | — | 0.05 |
| gantrez | — | 2 |
| PEG 300 | 4.5 | 4.45 |
| glycerin | 20 | 20 |
| flavor | 1 | 1 |
| SLS | 1.5 | 1.5 |
| NaF | 0.24 | 0.24 |
| Saccharin | 0.3 | 0.3 |
| Aq. Buffer, pH 7.0 | 48.5 | 46.5 |
| Total | 76.54 | 76.54 |

We measure the activity of these dentifrices against biofilm formation by *A. viscosus* an organism that we have found to be relatively resistant to Compound 1 compared to many other biofilm-forming bacteria. G7 has very good efficacy, inhibiting the biofilm in this assay to the same extent as commercial Total® toothpaste with triclosan, whereas G5 is only slightly better than the control. Thus the addition of Gantrez (methyl vinyl ether-maleic acid copolymer or PVM/MA copolymer) significantly increases the activity of Compound A against biofilm formation by *A. viscosus*.

EXAMPLE 7

Optimization of Dentifrice

|  | G | H | I |
|---|---|---|---|
| Compound 1 | 0.75 | 0.75 | 0.75 |
| Sodium fluoride | 0.243 | 0.243 | 0.243 |
| 99.0-101.0% vegetable glycerin | 30.84 | 20.84 | 40.84 |
| Demineralized water | qs | qs | qs |
| Gantrez S-97 | 15 | 15 | 15 |
| Dental type Silica - Zeodent 105 - high cleaning silica | 10 | 10 | 10 |
| Dental type silica abrasive (Zeodent 115) | 8.5 | 8.5 | 8.5 |
| Polyethylene glycol 300 | 6.72 | 6.72 | 6.72 |
| Dental type silica - Zeodent 165-synth. amorphous ppt silica | 2.5 | 2.5 | 2.5 |
| Sodium Lauryl Sulfate powder | 1.5 | 1.5 | 1.5 |
| Sodium hydroxide 50% solution | 1.2 | 1.2 | 1.2 |
| Sodium CMC-12 | 1.0 | 1.0 | 1.0 |
| Flavor K91-6507 | 1.0 | 1.0 | 1.0 |
| Titanium dioxide | 0.75 | 0.75 | 0.75 |
| Tetrasodium pyrophosphate - fine | 0.5 | 0.5 | 0.5 |
| Xanthan gum | 0.5 | 0.5 | 0.5 |
| Sodium saccharin | 0.3 | 0.3 | 0.3 |
| Sodium ascorbyl phosphate or dl-α-tocopherol | 0.2 | 0.2 | 0.2 |
| Sucralose | 0.15 | 0.15 | 0.15 |
| Butylated hydroxytoluene | 0.03 | 0.03 | 0.03 |

These formulations are measured for inhibition of grown of *A. viscosus* over 24 hours, growth being measured as optical density at 610 nm. The value after 24 hrs for water or formulation G without Compound 1 was >1.4, compared to <0.2 for formulation G with Compound 1. This shows very good efficacy against this organism, as good or better than the positive control, commercial Total® toothpaste with triclosan. Similarly, in a multispecies biofilm assay, the CFU mean for formulation G and for Total® was <2 (SD 0) compared to $1.1 \times 10^9$ (SD $1.5 \times 10^8$), showing that toothpaste containing Compound 1 is capable of inhibiting biofilm formation.

EXAMPLE 8

Use of Chelating Agent

It is observed that a silica-based dentifrice quickly changes color from white to yellow upon addition of 0.25-1% of Compound 1 in the final step of the formulation. This color change is observed with or without presence of an antioxidant, such as butylated hydroxytoluene (BHT), vitamin E or vitamin C. The addition of a small amount of a metal chelating agent, however, returns the dentifrice to its original white color. Chelating agents effective for this purpose include 0.5% Tetrasodium pyrophosphate (TSPP), as well as tetrapotassium pyrophosphate, ethylene diamine tetraacetic acid, ethylene glycol tetraacetic acid, sodium pyrophosphate, sodium tripolyphosphate, potassium tripolyphosphate, sodium hexamephosphate, and citric acid.

EXAMPLE 9

Use of Antioxidants

Borinic esters can be oxidized by molecular oxygen or peroxides that can be formed from ethers such as PEG by the action of oxygen in the air. These highly oxidative species can attack the carbon-boron bond leading to cleavage and formation of corresponding boronic acid derivatives and phenol derivatives. The oxidation products are then inactive. Addition of oxygen scavengers and/or antioxidants such as vitamins C (ascorbic acid), vitamin E (α-tocopherol) or 2,6-di-tert-butyl-4-methyl-phenol (butylated hydroxytoluene or BHT) eliminates the oxygen and reduces the peroxides already present in the formulation. The amount of antioxidant does not need to exceed the amount of borinic ester used in a given formulation.

The stability of three formulations of Compound 1 are compared, the formulations being identical except that one is without any antioxidants, one contains α-tocopherol, and the third contains sodium ascorbylphosphate. Decomposition of formula I is significantly reduced the formulation containing sodium ascorbylphosphate, and is even less in the formulation containing α-tocopherol. This demonstrates that the use of an antioxidant enhances the stability of Compound 1 in formulation.

What is claimed is:

1. An oral care composition having a pH of 8.5-10, comprising a compound of formula A:

Formula A wherein the compound of Formula A is a compound of Formula (I)

Formula 1 wherein

R* and R** are independently substituted or unsubstituted aralkyl, substituted or unsubstituted aryl, substituted or unsubstituted cycloalkyl, or substituted or unsubstituted heterocycle;

z is 0 or 1, with the proviso, that if z is 1, then A is $CR^{10}$ or N, and D is N or $CR^{12}$, and with the further proviso that if z is 0 then D is O, S or $NR^{12a}$;

E is hydrogen, hydroxy, alkoxy, (cycloalkyl)oxy, (cycloheteroalkyl)oxy, carboxy, or alkyloxycarbonyl;

m is 0 or 1;

$R^{12}$ is hydrogen, hydroxyalkyl, aminoalkyl, alkylaminoalkyl, dialkylaminoalkyl, carboxy, alkyloxycarbonyl, amido, hydroxy, alkoxy, aryloxy, thio, alkylthio, arylthio, alkylsulfonyl, dialkylaminosulfonyl, alkylaminosulfonyl, aminosulfonyl, sulfo, cyano, halo, nitro, amino, dialkylamino, alkylamino, arylamino, diarylamino, aralkylamino, or diaralkylamino;

$R^{12a}$ is hydrogen, substituted or unsubstituted alkyl, substituted or unsubstituted heteroalkyl, substituted or unsubstituted aralkyl, substituted or unsubstituted aryl, substituted or unsubstituted cycloalkyl, or substituted or unsubstituted heterocycle; and $R^9$ and $R^{10}$ are independently hydrogen, alkyl, cycloalkyl, hydroxyalkyl, aminoalkyl, alkylaminoalkyl, dialkylaminoalkyl, halo, carbonyl, hydroxyimino, carboxy, alkyloxycarbonyl, alkylthio, alkylsulfonyl, arylthio, dialkylaminosulfonyl, alkylaminosulfonyl, aminosulfonyl, amino, alkoxy, nitro, sulfo, or hydroxy;

in free or pharmaceutically acceptable salt form.

2. The composition of claim 1 comprising 3-hydroxypyridine-2-carbonyloxy-bis(3-chloro-4-methylphenyl)-borane.

3. The composition of claim 1, wherein the orally acceptable carrier comprises water and a humectant and further comprising a buffer.

4. The composition of claim 3 further comprising one or more of arginine in free or pharmaceutically acceptable salt form, an antioxidant, a solubilizing agent and/or a chelator.

5. A composition according to claim 1 having a pH of at least 8 comprising an antibacterially effective amount of a compound of Formula (A); an antioxidant in an amount effective to inhibit the oxidation of the compound of Formula (A); a solubilizing agent; and an orally acceptable carrier.

6. The composition of claim 5 wherein the compound of formula (A) is present in an amount of 0.05% to 20% by weight.

7. The composition of claim 6 wherein the antioxidant is selected from ascorbic acid, sodium ascorbyl phosphate, butylated hydroxytoluene (BHT), alpha tocopherol, citric acid, or a mixture thereof and the composition has a pH of 8.5-10.

8. The composition of claim 7 wherein the solubilizing agent is a nonionic surfactant.

9. The composition of claim 8, wherein the nonionic surfactant is a copolymer of ethylene glycol and propylene glycol; a polyol; or polyethylene glycol.

10. The composition of claim 9 wherein the compound of Formula (A) is 3-hydroxypyridine-2-carbonyloxy-bis(3-chloro-4-methylphenyl)-borane.

11. The composition of claim 3 wherein the buffer is a phosphate buffer.

12. The composition of claim 11, further comprising a fluoride ion source and an abrasive.

13. The composition of claim 8, which further comprises a buffer and a polyvinylmethyl ether/maleic acid copolymers.

14. The composition of claim 13, wherein the buffer is a phosphate buffer.

15. The composition of claim 14, further comprising a fluoride ion source and an abrasive.

16. A method for preparing an oral care composition according to claim 1 comprising mixing a compound of Formula A with an orally acceptable carrier and adjusting or maintaining the pH at a level of at least 7.

17. A method to reduce, inhibit, or treat oral microbial infections comprising applying the composition of claim 1 to the oral cavity of a patient in need thereof.

18. A method to reduce or inhibit formation of dental caries, to treat, reduce or inhibit gingivitis, to reduce levels of oral bacteria, to inhibit microbial biofilm formation in the oral cavity, to reduce plaque accumulation, and/or clean the teeth and oral cavity, comprising applying a composition according to claim 1 to the teeth and gums of a subject in need thereof.

* * * * *